United States Patent [19]
Bacich et al.

[11] Patent Number: 5,376,084
[45] Date of Patent: Dec. 27, 1994

[54] CATHETER WITH INTERNAL MANDREL AND METHOD

[75] Inventors: Steven R. Bacich, Laguna Niguel; Guy R. Lowery, Mission Viejo; David P. Schickling, Laguna Hills; Girma A. Kebede, Mission Viejo, all of Calif.

[73] Assignee: Imagyn Medical, Inc., Laguna Niguel, Calif.

[21] Appl. No.: 779,356

[22] Filed: Oct. 17, 1991

[51] Int. Cl.⁵ .......................................... A61M 25/00
[52] U.S. Cl. .................................................. 604/281
[58] Field of Search ................ 604/95, 158, 159, 280, 604/281, 282, 283, 55

[56] References Cited

U.S. PATENT DOCUMENTS

| | | |
|---|---|---|
| 3,270,641 | 9/1966 | Gosselin . |
| 3,332,424 | 7/1967 | Minteer ................... 604/280 |
| 3,539,034 | 11/1970 | Tafeen . |
| 3,605,725 | 9/1971 | Bentov . |
| 3,867,945 | 2/1975 | Long . |
| 4,033,331 | 7/1977 | Guss et al. ............ 604/281 |
| 4,207,872 | 6/1980 | Meiri et al. . |
| 4,304,231 | 12/1981 | Bodicky et al. . |
| 4,416,660 | 11/1983 | Datoe ..................... 604/55 |
| 4,606,336 | 8/1986 | Zeluff ..................... 604/55 |
| 4,676,249 | 6/1987 | Arenas et al. ......... 604/282 |
| 4,781,681 | 11/1988 | Sharrow et al. ...... 604/280 |
| 4,813,930 | 3/1989 | Elliott . |
| 4,874,360 | 10/1989 | Goldberg et al. ..... 604/281 |
| 4,906,230 | 3/1990 | Maloney et al. . |
| 4,935,017 | 6/1990 | Sylvanowicz ......... 604/281 |
| 4,946,440 | 8/1990 | Hall . |
| 4,976,688 | 12/1990 | Rosenblum ............ 604/95 |

FOREIGN PATENT DOCUMENTS 0363661 4/1990 European Pat. Off. .

OTHER PUBLICATIONS

"Hysterosalpingography & Selective Salpingography", Cook OB/GYN, A Division of Cook Urological Inc. 1988.
"Catheterisation of the Fallopian Tubes From The Vagina", *The Lancet*, Robert P. S. Jansen et al, Aug. 8, 1987, pp. 309, 310.
"The Transvaginal Intratubal Transfer", O. Bauer et al, *Annals New York Academy of Sciences*, pp. 467–477.
"Medical Intelligence" Nonoperative Embryo Transfer To The Fallopian Tube; Robert P. S. Jansen, M. D. et al; reprinted from the *New England Journal of Medicine*, vol. 319, pp. 288–291, Aug. 4, 1988.

*Primary Examiner*—C. Fred Rosenbaum
*Assistant Examiner*—Manuel Mendez
*Attorney, Agent, or Firm*—Gordon L. Peterson

[57] ABSTRACT

A catheter comprising an elongated, flexible catheter body having a distal end portion which is curved in an unstressed condition. The catheter body has a through lumen and a mandrel lumen. A mandrel is provided in the mandrel lumen, and the mandrel has a distal end portion configured to at least partially straighten the curve of the distal end portion of the catheter body. The mandrel is movable between an extended position in which the mandrel at least partially straightens the curve of the distal end portion of the catheter body and a retracted position in which the catheter body is more curved than in the extended position of the mandrel.

31 Claims, 5 Drawing Sheets

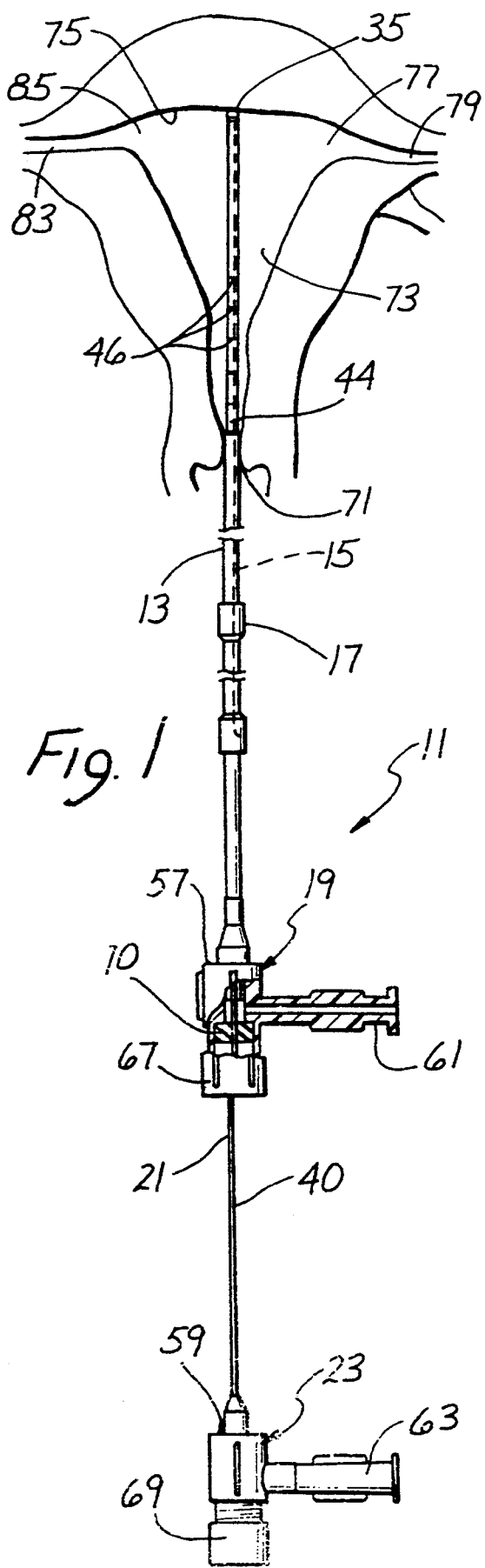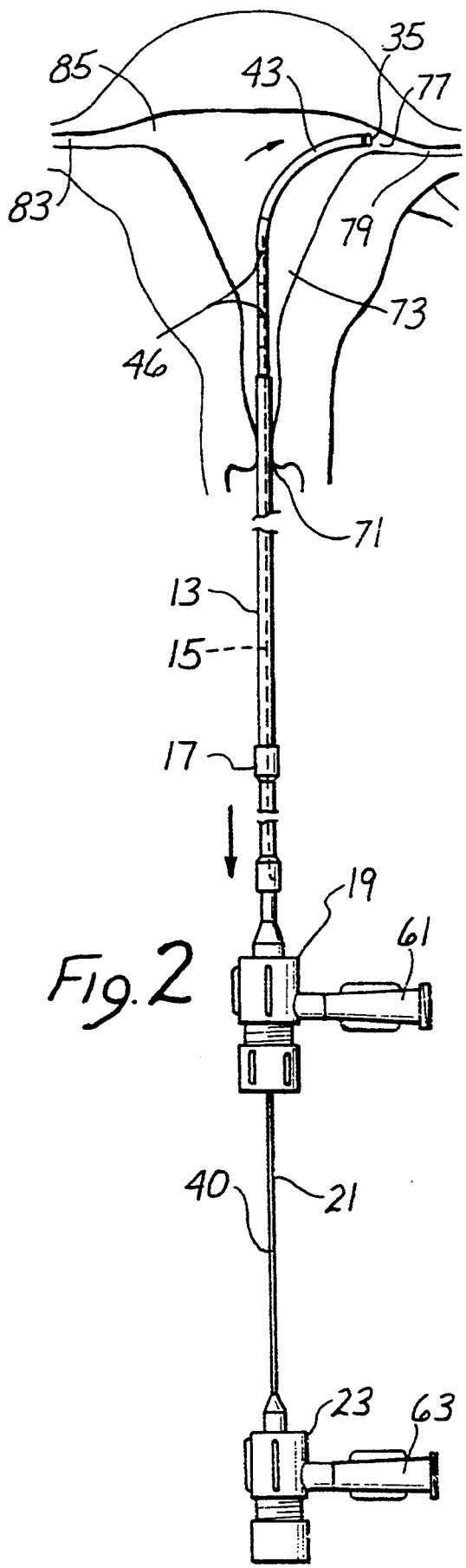

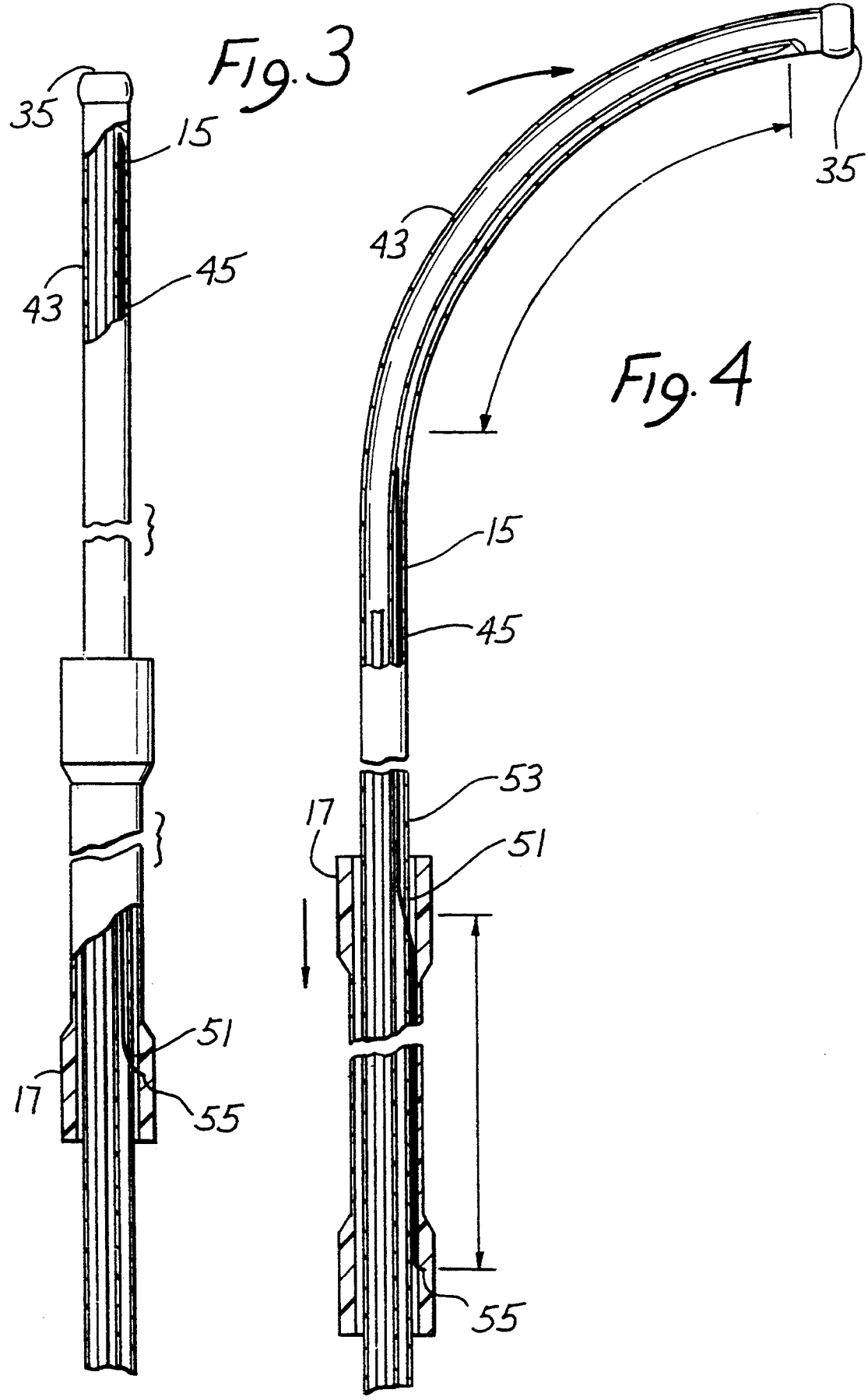

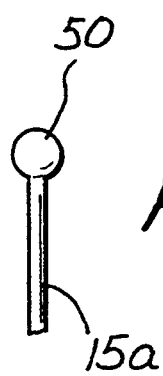
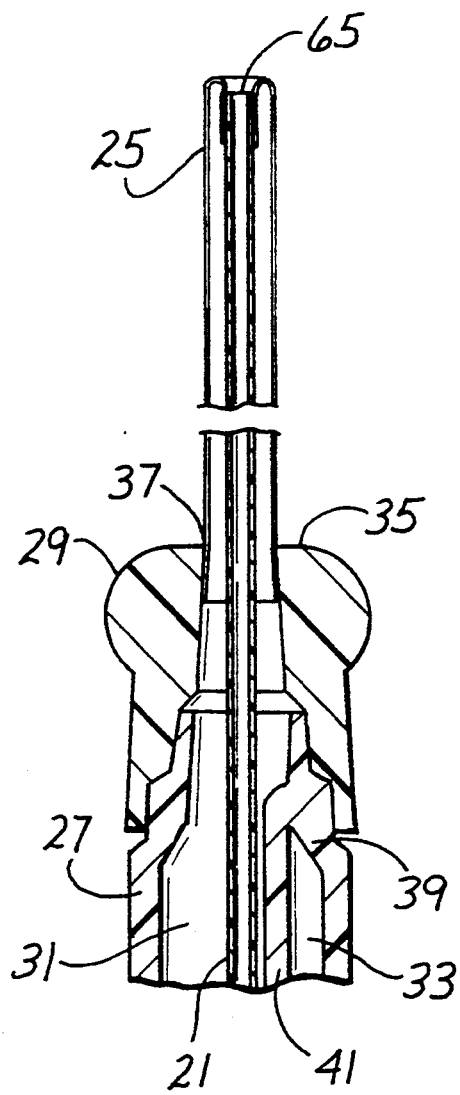
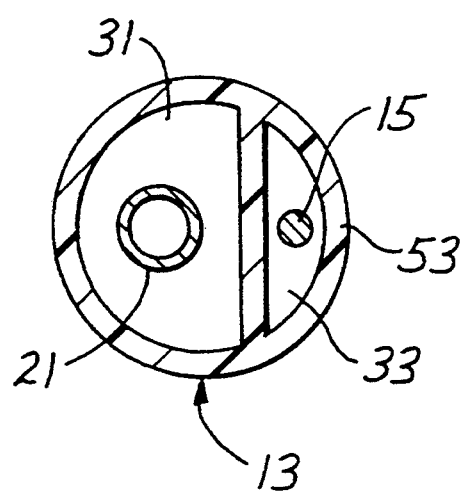

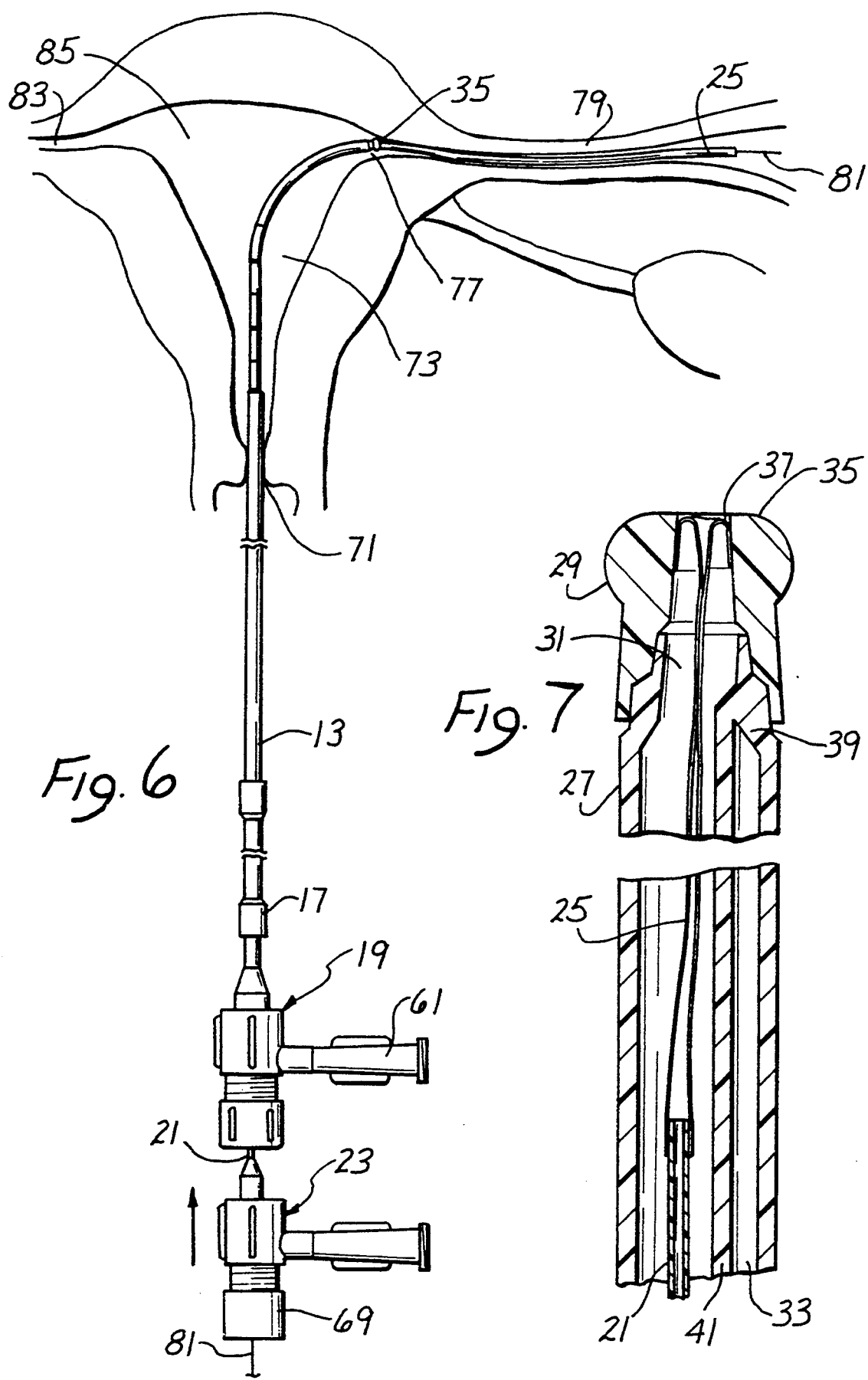

CATHETER WITH INTERNAL MANDREL AND METHOD

BACKGROUND OF THE INVENTION

Medical procedures often require obtaining access to internal regions of the body. For this purpose, it is common to use a catheter inserted through either a natural body orifice or through an incision. One example is in coronary angioplasty in which a catheter is inserted through the femoral artery to the desired region of the heart where the angioplasty procedure is carried out. Typically, the catheter has a preshaped distal end portion of a configuration designed to facilitate reaching the desired region of the heart. During insertion of the catheter, a guide wire is used, and the guide wire straightens the preshaped distal end portion. However, once the catheter is near the desired location, the wire is removed so the distal end portion of the catheter can return to its preformed shape to facilitate access to the desired coronary artery.

A similar approach is used in catheterizing the fallopian tubes utilizing a transcervical approach. For example, it may be necessary or desirable to access the fallopian tubes for the infusion of a contrast dye for fluoroscopic evaluation, the placement of another catheter in which embryos, zygotes or other genetic material are deposited within the fallopian tubes, the canulation of guide wires for tubal occlusions and the insertion of an endoscope.

One prior art approach utilizes a single-lumen catheter having a curved distal end portion in the unstressed condition. To insert the catheter, a mandrel is passed through the through lumen to straighten and stiffen the catheter. In this straightened and stiffened condition, the catheter is passed through the cervix, and the catheter is oriented in the direction of the desired ostium. Once oriented, the mandrel is removed completely from the catheter, and this allows the catheter to return to its preformed, curved shape. A medical procedure can then be carried out through the lumen.

If procedures must be carried out in both fallopian tubes, it is necessary to reinsert the mandrel through the lumen to straighten the catheter, reorient the catheter with respect to the other ostium, withdraw the mandrel and then carry out the desired procedure. Alternatively, the catheter used for the first fallopian tube may be withdrawn and a second catheter may be utilized for the second fallopian tube.

One problem with this procedure is that the mandrel must be removed from the lumen and replaced with some other instrument in order to carry out the medical procedure, and this increases the time required. This replacement procedure also adds complexity and may require an additional staff member to complete. The procedure becomes even more time consuming and complex when both ostia must be accessed. In addition, if a second catheter is used for the second ostia, the cost of the procedure is increased. If the same catheter is removed, straightened and reinserted, there is an added danger of infection as a result of the reinsertion through the vaginal cavity.

It is also known to employ a pull wire to curve the distal end portion of a normally straight catheter. However, these catheters are not likely to have the rigidity required to pass through the cervix.

SUMMARY OF THE INVENTION

This invention reduces the time and complexity of a catheterization procedure of the type requiring the use of a mandrel to alter the shape of a preformed distal end portion of a catheter body. In addition, for certain procedures the risk of infection and cost are also reduced. Although this invention is particularly applicable to catheterization of a fallopian tube, some of the features of this invention have other applications.

This invention may be embodied in a catheter which includes an elongated, flexible catheter body having a distal end portion which is of a first configuration in an unstressed condition. The catheter body has a first lumen, which is typically a through lumen, that extends into the distal end portion and opens at a distal opening in the distal end portion. The catheter also includes a mandrel having a distal end portion of a second configuration which is different from the first configuration. The distal end portion of the mandrel has sufficient strength to alter the first configuration of the catheter body, and preferably it has sufficient strength to substantially conform the distal end portion of the catheter body to the second configuration.

One feature of this invention is that the catheter body has a separate mandrel lumen. The mandrel is movable in the mandrel lumen between an extended position in which the distal end portion of the mandrel is sufficiently within the distal end portion of the catheter body to alter the first configuration of the distal end portion of the catheter body and a retracted position in which the mandrel is located proximally of the position the mandrel occupies in the extended position, and the distal end portion of the catheter is altered less than in the extended position.

Because a separate mandrel lumen is used for the mandrel, the through lumen is unobstructed by the mandrel, and the mandrel can remain in the catheter during the entire procedure. With this arrangement, the mandrel need not be withdrawn in order for another instrument, such as an endoscope, to be inserted through the through lumen. Also, the mandrel can be easily re-employed to again alter the unstressed configuration of the distal end portion.

The unstressed first configuration of the distal end portion of the catheter can be any configuration which is required in order to access the desired body region. In a preferred embodiment which is particularly adapted for fallopian tube use, in an unstressed condition, the distal end portion of the catheter body is deflected with respect to a contiguous region of the catheter body. In this event, the mandrel has a distal end portion which is configured to alter this unstressed first configuration of the distal end portion of the catheter body. The deflection of the distal end portion of the catheter body may be provided by one or more curves or sharp bends in the same or different planes. For accessing the fallopian tubes, the unstressed or preformed configuration is preferably curved. The mandrel may partially or totally straighten the curve. In the case of fallopian tube access, the mandrel preferably substantially straightens the curve so that the catheter body is substantially straightened and stiffened for passage into the uterus. In the retracted position, the mandrel may exert substantially no effect on the shape of the distal end portion of the catheter body.

In order to facilitate manipulation of the mandrel, the catheter preferably includes a control slide mounted on the catheter body for movement longitudinally of the catheter body. By coupling the mandrel to the control slide, the control slide can move the mandrel between the extended and retracted positions. This can also be relatively easily accomplished with one hand thereby freeing the other hand of the physician for other tasks. In addition, the control slide facilitates accurate movement of the mandrel the precisely correct amount to achieve the desired distal end portion configuration for the catheter body.

To facilitate movement of the mandrel through the mandrel lumen along the distal end portion, the mandrel has a distal end and a distal region that terminates at the distal end. The distal region is deflected with respect to a contiguous region of the distal end portion of the mandrel in a way to facilitate movement of the mandrel along the distal end portion.

It is preferred to maintain the distal region of the mandrel and the distal end portion of the catheter body in substantially the same planar region. Although this can be accomplished in different ways, preferably the attachment of the mandrel to the control slide also serves to accomplish this function.

The distal region of the mandrel may have various different configurations. For some applications, it may desirable to employ a mandrel which terminates distally in an enlarged, round tip.

In a preferred construction, the catheter body has a peripheral wall with an opening proximally of the distal end portion of the catheter body. The opening leads to the mandrel lumen, and the mandrel exits through the opening. If the control slide is employed, it is preferably coupled to the mandrel at a proximal end of the mandrel which lies outside of the opening.

Preferably, the catheter includes means for preventing the mandrel from being completely withdrawn from the mandrel lumen through the opening. In a preferred construction, such means includes the control slide and the attachment of the mandrel to the control slide. However, such means may take other forms, such as a stop on the mandrel which prevents its full withdrawal through the opening whether such opening is on the peripheral wall of the catheter body or at the proximal end of the catheter body.

The movement of the mandrel longitudinally within the mandrel lumen is preferably limited by stops. The rear or proximal stop prevents complete withdrawal of the mandrel from the mandrel lumen. The forward or distal stop limits the forward or distal movement of the mandrel. This is important to assure that the mandrel does not project beyond the distal end of the catheter body where it could injure the patient. Preferably, the mandrel lumen terminates distally in an end wall which would also tend to prevent extension of the mandrel distally beyond the distal end of the catheter body. However, even if the end wall is provided, the distal stop prevents movement of the mandrel distally to a position in which the mandrel would contact the end wall.

Although this invention can be used in different kinds of catheters, it is particularly adapted for an everting catheter. An everting-type catheter is characterized by an elongated inner member having a distal end portion and a flexible everting element coupled to the distal end portions of the inner member and the catheter body. The provision of a dedicated, separate mandrel lumen is particularly important in this type of catheter to assure that the mandrel does not rupture the thin, flexible everting element.

According to a method feature of this invention, the distal end portion of the catheter, which has been substantially straightened by the mandrel, is inserted through the cervix and into the uterus. The mandrel is then retracted to the retracted position without removing the mandrel from the mandrel lumen to allow the distal end portion of the catheter body to assume its unstressed configuration. The distal opening of the through lumen is then directed toward one ostium, and a medical procedure, which may involve examination and/or treatment, is carried out through the through lumen in the fallopian tube associated with that ostium.

If both ostia are involved, the mandrel is advanced to the extended position without withdrawing the catheter body from the uterus, and the catheter body is oriented generally about its longitudinal axis. The mandrel is then retracted to the retracted position without removing the mandrel from the mandrel lumen and without withdrawing the catheter body from the uterus. The distal opening of the through lumen is then directed toward the other ostium, and a procedure, which may involve examination and/or treatment, is carried out in the fallopian tube associated with that ostium utilizing the through lumen. With this method, both ostia are accessed with a single catheter without having to withdraw either the mandrel from the catheter body or the catheter from the uterus.

The invention, together with additional features and advantages thereof may best be understood by reference to the following description taken in connection with the accompanying illustrative drawing.

BRIEF DESCRIPTION OF THE DRAWINGS.

FIG. 1 is a plan view of a catheter constructed in accordance with the teachings of this invention with the catheter body being straightened and inserted into the uterus of a patient.

FIG. 2 is a plan view similar to FIG. 1 with the distal end portion of the catheter in the curved configuration.

FIG. 3 is an enlarged, fragmentary view partially in section of a portion of the catheter with the catheter body being in a straightened condition.

FIG. 4 is a view similar to FIG. 3, with the catheter body being in the curved configuration.

FIG. 4A is an enlarged, fragmentary side elevational view of a distal segment of a mandrel of an alternate configuration. FIG. 5 is an enlarged, fragmentary, sectional view taken generally along line 5—5 of FIG. 3.

FIG. 6 is a plan view similar to FIG. 1 with the everting element everted into one of the fallopian tubes.

FIG. 7 is an enlarged, fragmentary, sectional view taken on a longitudinal plane of a distal region of the catheter and with the everting member inverted within the catheter body.

FIG. 8 is a sectional view similar to FIG. 7 with the everting element everted out of the distal end of the catheter body.

DESCRIPTION OF THE PREFERRED EMBODIMENT

Figure 9:
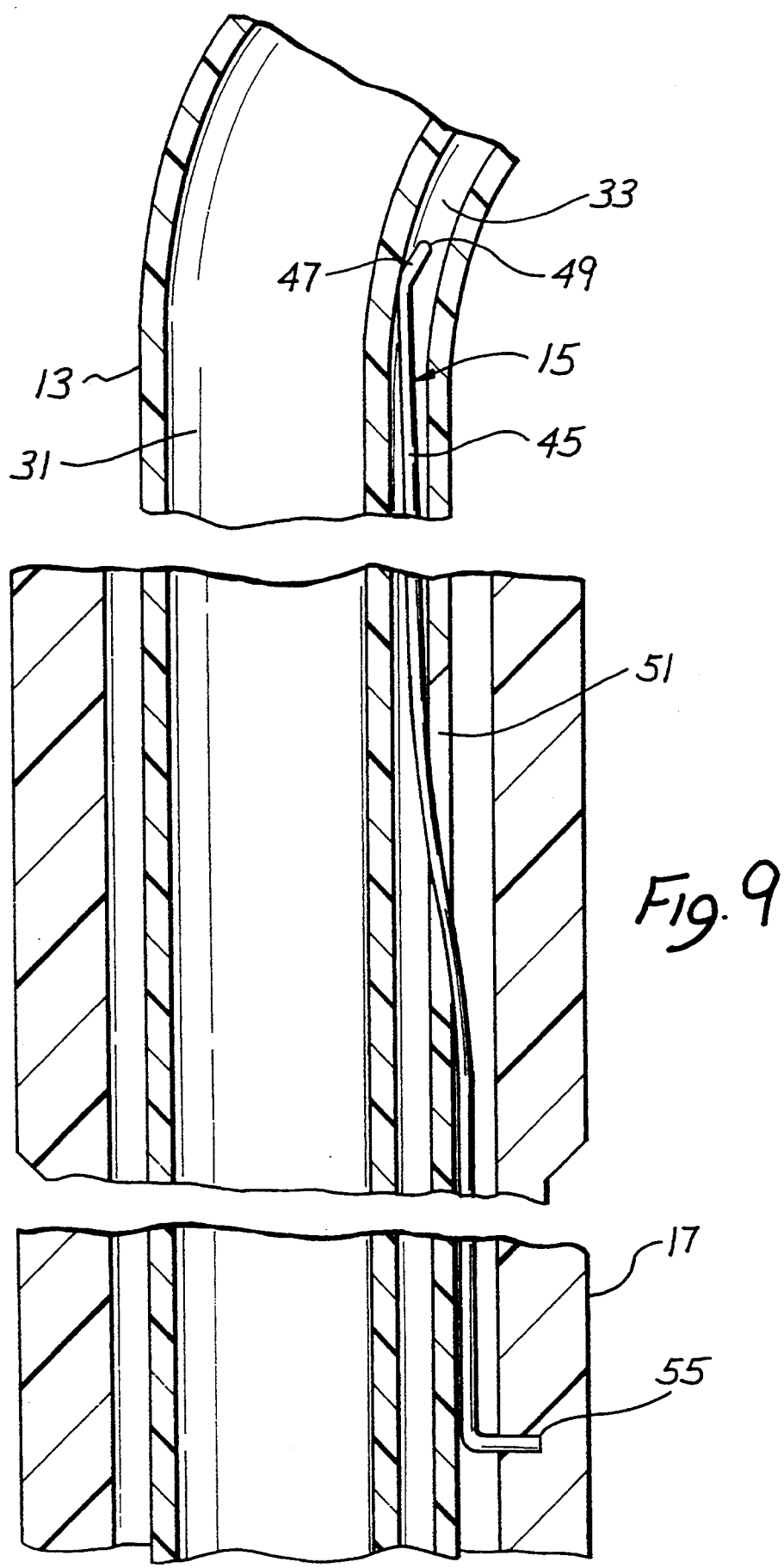
FIG. 9 is an enlarged, fragmentary sectional view taken on an axial plane with the mandrel in the retracted position.

FIG. 1 shows a catheter 11 which generally comprises a catheter body 13, a mandrel 15 (FIGS. 1-5), a control slide 17, a catheter body fitting 19, an inner member in the form of an inner catheter tube 21, an inner tube fitting 23 and an everting element 25 (FIGS. 7 and 8). The catheter body 13 is elongated and flexible and includes a main body 27 (FIGS. 7 and 8) and a tip member 29 affixed to the distal end of the main body. The catheter body 13, which may be lumen 33. The through lumen 31 extends all the way through the catheter body 13 from a proximal end of the catheter body at the catheter body fitting 19 to a distal end 35 (FIGS. 7 and 8) where the through lumen opens at a distal opening 37. The mandrel lumen 33 terminates in an end wall 39 (FIGS. 7 and 8). The lumens 31 and 33 are preferably, but not necessarily, completely isolated from each other by a wall 41 (FIGS. 5, 7 and 8)

Although various constructions are possible, the tip member 29 is preferably bonded to the main body 27 (FIGS. 7 and 8). The entire catheter body 13 is constructed of a suitable biocompatible material. For example, the main body 27 may be constructed of a flexible, biocompatible polymeric material, such as nylon, polyethylene, polyurethane or silicone. The tip member 29 is preferably constructed of a soft, biocompatible polymeric material, such as silicone.

The catheter 11 is a linear everting catheter, and as such, includes not only the inner tube 21, but also the thin, flexible everting element 25. The everting element 25 is bonded to the distal end portion of the inner tube 21 and to an inner surface of the tip member 29 as shown in FIGS. 7 and 8. This causes the everting element 25 to fold as shown in these figures adjacent the distal end portion of the inner tube 21. Linear everting catheters are known, and the manner of attachment of the everting element 25 to the inner tube 21 and the tip member 29 may be carried out in accordance with known procedures. Similarly, the everting element 25 and the inner tube 21 can be moved between the positions of FIGS. 7 and 8 by controlling the pressure within the everting element 25 while simultaneously manually moving the inner tube 21 in a manner known in the art.

The inner tube 21 may be of various different constructions. However, the inner tube 21 preferably has a relatively rigid proximal section 40 (FIGS. 1 and 2), which may be constructed of stainless steel, and a flexible distal section 42 (FIG. 8) which is constructed of a suitable biocompatible, flexible polymeric material. The sections 40 and 42 are suitably joined together as by an adhesive at a location 44 (FIG. 1) so that at least the portion of the inner tube 21 which extends through the curved, distal end portion 43, which is described below, is flexible. The precise position of the location 44 is not critical.

The catheter body 13 has a distal end portion 43 of a preformed configuration. In the illustrated embodiment, the preformed configuration is different from the configuration of the region of the catheter body 13 which is contiguous to the distal end portion 43 and is deflected with respect to such region. In the specific embodiment illustrated, the distal end portion 43 is curved in an unstressed condition. More specifically, in the illustrated embodiment, the curve forms a portion of a circular arc which may extend through, for example, up to about 90 degrees. In the drawings, the arc through which the curve extends approximates 90 degrees, but this is merely illustrative as an arc of 65 to 75 degrees is also suitable as are arcs of other lengths. The curve may be provided to the distal end portion 43 in any conventional way, such as by utilizing a thermoplastic material for the catheter body 13, heating the distal end portion in a mold or die of the desired shape and then cooling the distal end portion. If a thermosetting plastic is used, the distal end portion 43 can be molded to the desired configuration. Of course, the distal end portion 43 may be constructed integrally with the remainder of the catheter body 13 or as a separate member and then attached to the remainder of the catheter body 13. The catheter body 13 has a series of longitudinally spaced, annular depth markings 46.

The mandrel 15' is an elongated, flexible member which may be constructed, for example, of 304 series stainless steel spring-tempered wire. Although the mandrel 15 is flexible, it possesses sufficient rigidity to alter, and in this specific embodiment, straighten the preformed configuration of the distal end portion 43 of the catheter body 13.

The mandrel 15 has a distal end portion 45 which is configured to alter and, in the illustrated embodiment, straighten the distal end portion 43 of the catheter body 13. The distal end portion 45 of the mandrel 15 is straight and linear, except for a distal region 47 (FIG. 9) of the mandrel. The distal region 47 is angularly deflected with respect to the contiguous region of the distal end portion 45 of the mandrel 15. The mandrel 15 is within the mandrel lumen 33 and is movable longitudinally in that lumen between the extended position shown in FIGS. 1 and 3 and the retracted position shown in FIGS. 2, 4 and 9. The purpose for the angularly deflected distal region 47 is to facilitate movement of the mandrel 15 through the mandrel lumen 33 along the distal end portion 43 of the catheter body 13.

Although the mandrel 15 and the distal region 47 thereof can be of various different constructions depending on the cross-sectional area of the mandrel lumen 33, stiffnesses of the mandrel 15 and the catheter body 13 and the shape of the distal end portion 43 in the unstressed condition, in one preferred construction, the mandrel has a diameter of about 0.022 inch, and the distal region has a length of no greater than about 0.080 inch and no less than about 0.020 inch. Lengths greater than 0.080 inch tend to undesirably increase the friction between the distal region 47 and the wall of the mandrel lumen 33, and lengths under 0.020 inch tend to reduce the benefit of the deflected distal region 47. Although the distal region 47 can be curved, preferably, it is simply bent through an angle with respect to the contiguous portion of the mandrel 15. This angle is preferably at least about 15 degrees in order to provide the reduced friction benefit and preferably not over 45 degrees because angles greater than 45 degrees tend to require a larger cross-sectional area mandrel lumen 33 than is desired. To further facilitate movement of the mandrel 15 through the curved portion of the mandrel lumen 33, the mandrel 15 preferably terminates in a rounded, full radius, ball-like distal end 49 and is coated with low-friction material, such as a silicone or Teflon.

FIG. 4A shows a mandrel 15a which is identical to the mandrel 15 in all respects not shown or described herein. The only difference between the mandrels 15 and 15a is that the latter has an enlarged, rounded distal tip 50 in lieu of the deflected distal region 47. In the form shown in FIG. 4A, the distal tip 50 is essentially spherical and forms a ball; however, other rounded configurations, such as tear drop or olive configurations may also be used.

The catheter body 13 has an opening 51 (FIGS. 4 and 9) in its peripheral wall 53 with the opening being proximally of the distal end portion 43. The opening 51 leads to the mandrel lumen 33, and the mandrel 15 extends through the opening 51 as shown in FIGS. 4 and 9 whereby the mandrel extends to the exterior of the catheter body 13. The mandrel 15 has a proximal segment 55 which extends radially outwardly and is received in a corresponding recess in the control slide 17.

The attachment of the mandrel 15 to the control slide 17 accomplishes two important results. First, by moving the control slide 17 longitudinally on the catheter body 13, the mandrel 15 can be moved between the extended position of FIGS. 1 and 3 and the retracted position of FIGS. 2, 4 and 9. Moreover, this movement can be easily accomplished using only one hand of the physician. Secondly, the attachment of the mandrel 15 to the control slide 17 prevents rotation of the mandrel 15 about its longitudinal axis so that the distal region 47 cannot rotate substantially out of the planar region in which it is placed. Accordingly, this enables the distal end portion 43 of the catheter body 13 and the distal region 47 of the mandrel 15 to be retained in substantially the same planar region. By maintaining this orientation, the deflected distal region 47 is better able to travel through the curved mandrel lumen 33.

Although the control slide 17 can be of various different configurations, in the illustrated embodiment, it is a tubular member which slidably receives the catheter body 13. The catheter body fitting 19 forms a stop which limits the travel of the control slide 17 proximally to thereby prevent the mandrel 15 from being completely withdrawn from the mandrel lumen 33 through the opening 51. Thus, the mandrel 15 is an integral part of the catheter 11. Of course, other forms of stops can be provided, such as an enlargement on the mandrel 15 which is too large to pass through the opening 51. Similarly, the movement of the control slide 17 distally is also limited, and in this embodiment, it is limited by the mandrel 15 and the opening 51 reaching the position shown in FIG. 3. It would not be possible without exerting excessive force to move the control slide 17 proximally of this position because it would require sharply doubling back of the mandrel 15 on itself. Of course, other forms of stops, including a hard stop on the catheter body, can be used to limit proximal movement of the control slide 17.

In the illustrated embodiment, the opening 51 is in the form of a circumferentially narrow hole having a short dimension so that the mandrel 15 will easily pass through the opening. However, if desired, the opening 51 may be in the form of a much longer elongated slot, and in this event, the direction of elongation of the slot may be in the direction of elongation of the catheter body 13.

The fittings 19 and 23 may each be in the form of T-adapters, and they have legs 57 and 59, respectively, which are coupled to the proximal ends of the catheter body 13 and the inner tube 21, respectively. The fittings 19 and 23 also have injection legs 61 and 63, respectively, for the injection of an appropriate media. The media injected through the legs 61 and 63 may be either a liquid or a gas. For example, the media that is injected through the leg 61 may be an inflation media for inflating the everting element 15 or a contrast media. The leg 63 can be used, for example, for irrigation fluid, a contrast dye, drugs or for aspiration. In this regard, any media infused through the leg 63 passes through the inner tube 21 and out through the distal end 65 (FIG. 8) of the inner tube. The media injected through the leg 61 enters the through lumen 31 outside of the inner tube 21 and travels to the everting element 25 (FIGS. 7 and 8).

The fittings 19 and 23 have third legs 67 and 69, respectively. The third leg 67 has a seal 70 which prevents the media injected through the leg 61 from passing out through the leg 67 and which provides a sliding fit with the inner tube 21 to allow it to be moved along with the fitting 23 both proximally and distally with respect to the fitting 19. The leg 69 provides a port for the introduction of any of a variety of medical instruments such as an endoscope for viewing of the fallopian tubes. Both of the fittings 19 and 23 may be conventional.

In use of the catheter 11, the control slide 17 is moved distally to the position of FIGS. 1 and 3 to move the mandrel 15 through the curved portion of the mandrel lumen 33 to the extended position in which the mandrel straightens, or substantially straightens, the distal end portion 43 of the catheter body to provide the substantially straightened catheter body shown in these figures. Next, the distal end portion 43 of the substantially straightened catheter body 13 is inserted through the cervix 71 of a patient into the uterus 73 to the position shown in FIG. 1 in which the distal end 35 contacts or is near the fundus 75. The depth markings 46 reveal the depth of insertion of the catheter body 13. The mandrel 15 not only straightens the curved distal end portion 43, but also provides added rigidity to the distal end portion 43 for the insertion process.

The mandrel 15 is then retracted in the mandrel lumen 33 to a retracted position shown in FIGS. 2 and 4 in which the mandrel is positioned proximally of the distal end portion 43. Consequently, the distal end portion 43 of the catheter body 13 is allowed to return to its naturally curved condition. This retraction of the mandrel 15 is carried out without removing the mandrel from the mandrel lumen 33. Also the distal end 49 of the mandrel 15 is sufficiently advanced within the catheter body 13 to be within the uterus even when it is in the retracted position so it can provide the desired rigidity for further manipulation of the catheter body 13 as may be desired.

Preferably, the insertion process is carried out so that, when the mandrel 15 is retracted, the distal end portion 43, and in particular the distal opening 37 of the through lumen 31, will be directed toward one ostium 77 of one of the fallopian tubes 79. However, the catheter body may be manipulated during or following the insertion step as by rotating the catheter body 13 about its longitudinal axis to bring about the desired orientation of the distal end 35 and the ostium 77.

To gain access to the fallopian tubes 79, the everting element 25 is everted as shown in FIG. 6 so it extends for a distance into the fallopian tube 79. The eversion of the everting element 25 is carried out in a known manner which includes introducing an inflation medium through the leg 61 into the interior of the everting element and advancing the fitting 23 and, hence inner tube 21, in the catheter body 13 as may be desired to control the eversion process in a known manner. With the fallopian tube 79 accessed in this manner, a medical procedure can be carried out in the fallopian tube through the through lumen 31. For example, an elongated, flexible endoscope 81 (FIG. 6) can be inserted through the leg 69 and inner tube 21 into the fallopian tube 79 for visual examination of the fallopian tube.

Upon completion of the medical procedure, the other fallopian tube 83 may be examined or treated, if desired, without withdrawing the catheter 11 from the uterus 73. To accomplish this, the mandrel 15 is advanced to the extended position shown in FIG. 1, and the catheter body 13 is rotated generally about the longitudinal axis of the catheter body for about 180 degrees so as to roughly orient the catheter with respect to the ostium 85 of the other fallopian tube 83. The mandrel 15 is then moved to the retracted position of FIGS. 2 and 4 to allow the distal end portion 43 of the catheter body 13 to assume its natural curve with the distal end 35 now pointing generally toward the ostium 85. The procedure described above with respect to the ostium 77 and the fallopian tube 79 is then repeated, although the same or a different medical procedure may be carried out within the fallopian tube 85.

Although an exemplary embodiment of the invention has been shown and described, many changes, modifications and substitutions may be made by one having ordinary skill in the art without necessarily departing from the spirit and scope of this invention.

We claim:

1. A catheter comprising:
    an elongated flexible catheter body having a distal end portion which is deflected with respect to a contiguous region of the catheter body in an unstressed condition;
    said catheter body having a first lumen and a mandrel lumen, said first lumen and said mandrel lumen extending into said distal end portion said catheter body having a mandrel opening;
    a mandrel receivable in said mandrel lumen and having a distal end portion configured to at least partially straighten the distal end portion of the catheter body;
    said mandrel including said distal end portion of said mandrel being movable in said mandrel lumen between an extended position in which the distal end portion of the mandrel is sufficiently within the distal end portion of the catheter body to at least partially straighten the distal end portion of the catheter body and a retracted position in which the mandrel is located proximally of the position the mandrel occupies in the extended position and the distal end portion of the catheter body is more deflected than in the extended position; and
    a control slide mounted on the catheter body for movement longitudinally of the catheter body and said mandrel extending through the mandrel opening and being coupled to the control slide whereby the control slide can move the mandrel between the extended and retracted positions.

2. A catheter as defined in claim 1 including an elongated inner member having a distal end portion, said inner member being in said first lumen and a flexible everting element coupled to the distal end portions of the inner member and the catheter body.

3. A catheter as defined in claim 1 wherein the distal end portion of the mandrel has a distal end and a distal region that terminates at the distal end, said distal region is deflected with respect to a contiguous region of the distal end portion of the mandrel to facilitate movement of the mandrel including said distal end portion of said mandrel in the mandrel lumen along the distal end portion of the catheter body.

4. A catheter as defined in claim 3 wherein the distal region of the mandrel and the distal end portion of the catheter body lie in substantially the same planar region.

5. A catheter as defined in claim 4 wherein said control slide holds the distal region of the mandrel in substantially the same planar region as the distal end portion of the catheter body.

6. A catheter as defined in claim 1 wherein the distal end portion of the mandrel is substantially straight, substantially straightens the distal end portion of the catheter body in the extended position and exerts substantially no effect on the shape of the distal end portion of the catheter body in the retracted position.

7. A catheter as defined in claim 1 including a catheter body fitting coupled to a proximal region of the catheter body wherein the catheter body has a peripheral wall, said mandrel opening proximally of the distal end portion of the catheter body and distally of the catheter body fitting, said opening leading to the mandrel lumen and the mandrel extends through the opening.

8. A catheter as defined in claim 7 including means for preventing the mandrel from being completely withdrawn from the mandrel lumen through the opening.

9. A catheter as defined in claim 1 including means for preventing complete withdrawal of the mandrel from the mandrel lumen.

10. A catheter as defined in claim 1 wherein the catheter body terminates distally in a distal end and the catheter includes a stop to prevent movement of the mandrel distally beyond the distal end of the catheter body.

11. A catheter as defined in claim 1 wherein the distal end portion of the catheter body is curved in the unstressed condition.

12. A catheter as defined in claim 1 wherein the mandrel terminates distally in an enlarged, rounded tip.

13. A catheter comprising:
    an elongated, flexible catheter body having a distal end portion which is curved in an unstressed condition and which terminates in a distal end;
    said catheter body having a through lumen and a mandrel lumen, said through lumen having a distal opening at said distal end and said mandrel lumen extending into said distal end portion;
    an elongated inner tube having a flexible distal end portion, said inner tube being in said through lumen;
    a flexible everting element coupled to the distal end portion of the catheter body and to the distal end portion of the inner tube;
    a mandrel receivable in said mandrel lumen and having a distal end portion configured to substantially straighten the curved distal end portion of the catheter body;
    said mandrel including said distal end portion of said mandrel being movable in said mandrel lumen between an extended position in which the distal end portion of the mandrel is sufficiently within the distal end portion of the catheter body to substantially straighten the curved distal end portion of the catheter body and a retracted position in which the mandrel is located proximally of the position the mandrel occupies in the extended position and the distal end portion of the catheter body is curved.

14. A catheter as defined in claim 13 including a control slide mounted on the catheter body for movement longitudinally of the catheter body and said mandrel is coupled to the control slide whereby the control slide can move the mandrel between the extended and retracted positions.

15. A catheter as defined in claim 13 wherein the distal end portion of the mandrel has a distal end, a distal region that terminates at the distal end and a substantially straight contiguous region contiguous the distal region, said distal region is deflected with respect to the contiguous region of the distal end portion of the mandrel to facilitate movement of the mandrel along the distal end portion in the mandrel lumen of the catheter body.

16. A catheter as defined in claim 15 wherein the distal region of the mandrel and the distal end portion of the catheter body lie in substantially the same planar region.

17. A catheter as defined in claim 16 including a control slide mounted on the catheter body for movement longitudinally of the catheter body and said mandrel is coupled to the control slide whereby the control slide can move the mandrel between the extended and retracted positions, and said control slide holds the distal region of the mandrel in substantially the same planar region as the distal end portion of the catheter body.

18. A catheter as defined in claim 17 wherein the catheter body has a peripheral wall with an opening proximally of the distal end portion of the catheter body leading to the mandrel lumen and the mandrel extends through the opening.

19. A catheter as defined in claim 18 including means for preventing the mandrel from being completely withdrawn from the mandrel lumen through the opening.

20. A catheter as defined in claim 13 including means for preventing the complete withdrawal of the mandrel from the mandrel lumen.

21. A catheter as defined in claim 13 wherein the mandrel terminates distally in an enlarged, rounded tip.

22. A method of gaining access to the fallopian tubes comprising:
providing a catheter which includes an elongated flexible mandrel and an elongated flexible catheter body having a distal end portion which is deflected with respect to a contiguous region of the catheter body in an unstressed condition, a through lumen having a distal opening and a mandrel lumen which extends into said distal end portion, said mandrel having a distal end portion configured to at least partially straighten the distal end portion of the catheter body;
with the mandrel in the mandrel lumen and in an extended position in which the mandrel substantially straightens the catheter body to provide a substantially straightened catheter body, inserting the distal end portion of the substantially straightened catheter body through the cervix and into the uterus;
retracting the mandrel including said distal end portion of said mandrel in the mandrel lumen without removing the mandrel from the mandrel lumen to a retracted position in which the distal end portion of the catheter body is deflected with respect to the contiguous region of the catheter body; and
directing the distal opening of the through lumen toward one ostium and carrying out a procedure through the through lumen in the fallopian tube associated with said one ostium.

23. A method as defined in claim 22 including advancing the mandrel to the extended position without withdrawing the catheter body from the uterus and rotating the catheter body generally about a longitudinal axis of the catheter body, retracting the mandrel including said distal end portion of said mandrel to the retracted position without withdrawing the catheter body from the uterus, directing the distal opening of the through lumen toward another ostium and carrying out a procedure through the through lumen in the fallopian tube associated with said another ostium.

24. A method as defined in claim 22 including everting an everting element of the catheter into the fallopian tube associated with said one ostium before carrying out said procedure in the fallopian tube associated with said one ostium.

25. A catheter comprising:
an elongated flexible catheter body having a distal end portion of a first configuration in an unstressed condition;
said catheter body having a first lumen and a mandrel lumen, said first lumen and said mandrel lumen extending into said distal end portion said catheter body having a mandrel opening;
a mandrel in said mandrel lumen and having a distal end portion of a second configuration which is different from said first configuration, the distal end portion of the mandrel having sufficient strength to alter the first configuration of the catheter body;
said mandrel including said distal end portion of said mandrel being movable in said mandrel lumen between an extended position in which the distal end portion of the mandrel is sufficiently within the distal end portion of the catheter to alter the first configuration of the distal end portion of the catheter body and a retracted position in which the mandrel is located proximally of the position the mandrel occupies in the extended position and the distal end portion of the catheter body is less altered than in the extended position; and
a control slide mounted on the catheter body for movement longitudinally of the catheter body and said mandrel extending through the mandrel opening and being coupled to the control slide whereby the control slide can move the mandrel between the extended and retracted positions.

26. A catheter as defined in claim 25 including an elongated inner member having a distal end portion, said inner member being in said first lumen and a flexible everting element coupled to the distal end portions of the inner member and the catheter body.

27. A catheter as defined in claim 25 wherein the catheter body has a peripheral wall, said mandrel opening being in said peripheral wall proximally of the distal end portion of the catheter body leading to the mandrel lumen and the mandrel extends through the opening.

28. A catheter as defined in claim 25 including means for preventing complete withdrawal of the mandrel from the mandrel lumen.

29. A catheter as defined in claim 25 wherein the mandrel substantially conforms the distal end portion of the catheter body to said second configuration in the extended position.

30. A catheter as defined in claim 29 including a stop on the catheter body to limit travel of the control slide.

31. A catheter comprising:
an elongated flexible catheter body having a distal end portion which is deflected with respect to a contiguous region of the catheter body in an unstressed condition;

said catheter body having a first lumen and a mandrel lumen, said first lumen and said mandrel lumen extending into said distal end portion;

a mandrel receivable in said mandrel lumen and having a distal end portion configured to at least partially straighten the distal end portion of the catheter body;

said mandrel including said distal end portion of said mandrel being movable in said mandrel lumen between an extended position in which the distal end portion of the mandrel is sufficiently within the distal end portion of the catheter body to at least partially straighten the distal end portion of the catheter body and a retracted position in which the mandrel is located proximally of the position the mandrel occupies in the extended position and the distal end portion of the catheter body is more deflected than in the extended position; and the distal end portion of the mandrel having a distal end and a distal region that terminates at the distal end, said distal region being deflected with respect to a contiguous region of the distal end portion of the mandrel in the same direction as the distal end portion of the catheter body to facilitate movement of the mandrel in the mandrel lumen along the distal end portion of the catheter body.

* * * * *